United States Patent
Annegarn et al.

(10) Patent No.: US 12,011,258 B2
(45) Date of Patent: Jun. 18, 2024

(54) METHOD AND APPARATUS FOR DETERMINING A FALL RISK

(71) Applicant: Lifeline Systems Company, Framingham, MA (US)

(72) Inventors: Janneke Annegarn, Eidhoven (NL); Sietse Menno Rispens, Utrecht (NL); Warner Rudolph Theophile Ten Kate, Waalre (NL)

(73) Assignee: Lifeline Systems Company, Framingham, MA (US)

( * ) Notice: Subject to any disclaimer, the term of this patent is extended or adjusted under 35 U.S.C. 154(b) by 254 days.

(21) Appl. No.: 16/340,531

(22) PCT Filed: Oct. 10, 2017

(86) PCT No.: PCT/EP2017/075718
§ 371 (c)(1),
(2) Date: Apr. 9, 2019

(87) PCT Pub. No.: WO2018/069262
PCT Pub. Date: Apr. 19, 2018

(65) Prior Publication Data
US 2020/0046262 A1 Feb. 13, 2020

(30) Foreign Application Priority Data
Oct. 12, 2016 (EP) .................... 16193433

(51) Int. Cl.
*A61B 5/11* (2006.01)
(52) U.S. Cl.
CPC .......... *A61B 5/1117* (2013.01); *A61B 5/1118* (2013.01); *A61B 5/1122* (2013.01); *A61B 5/1123* (2013.01)

(58) Field of Classification Search
CPC .... A61B 5/1112; A61B 5/1113; A61B 5/1115; A61B 5/1116; A61B 5/1117;
(Continued)

(56) References Cited

U.S. PATENT DOCUMENTS

| | | | |
|---|---|---|---|
| 7,612,681 B2 | 11/2009 | Azzaro et al. | |
| 8,675,920 B2 | 3/2014 | Hanson et al. | |

(Continued)

FOREIGN PATENT DOCUMENTS

| | | | | |
|---|---|---|---|---|
| WO | 2009156936 A2 | 12/2009 | | |
| WO | WO-2009156936 A2 * | 12/2009 | ............. | G16H 30/40 |

(Continued)

OTHER PUBLICATIONS

Brodie et al: "Eight-Week Remote Monitoring Using a Freely Worn Device Reveals Unstable Gait Patterns in Older Fallers"; IEEE Transactions On Biomedical Engineering, vol. 62, No. 11, Nov. 2015, pp. 2588-2594.

(Continued)

*Primary Examiner* — May A Abouelela
*Assistant Examiner* — Anna Roberts
(74) *Attorney, Agent, or Firm* — Honigman LLP (57) ABSTRACT

According to an aspect, there is provided a computer-implemented method of determining a fall risk of a subject, the method comprising receiving a first data set indicative of movement of the subject; receiving a second data set indicative of context information of the subject; selecting a part of the first data set based on the second data set; and determining a fall risk based on the selected part of the first data set.

13 Claims, 6 Drawing Sheets

(58) Field of Classification Search
CPC .............. A61B 5/1118; A61B 5/1122; A61B 5/1123; A61B 5/1126; A61B 5/6802; A61B 5/7225; A61B 5/7246; A61B 5/7264; A61B 5/7275; A61B 5/7282; A61B 2560/0242; A61B 2560/0431; A61B 2562/0219; A61B 2562/06; G16H 50/20; G16H 50/30; G08B 21/043; G08B 21/0446

See application file for complete search history.

(56) References Cited

U.S. PATENT DOCUMENTS

| 10,835,186 | B2* | 11/2020 | Stone | A61B 5/1116 |
|---|---|---|---|---|
| 2008/0186189 | A1* | 8/2008 | Azzaro | G16H 15/00 340/573.7 |
| 2011/0190593 | A1 | 8/2011 | McNair | |
| 2011/0288811 | A1 | 11/2011 | Greene | |
| 2012/0119904 | A1 | 5/2012 | Coleman Boone et al. | |
| 2016/0220153 | A1* | 8/2016 | Annegarn | G08B 21/0446 |

FOREIGN PATENT DOCUMENTS

| WO | 2010026513 A1 | 3/2010 | |
|---|---|---|---|
| WO | 2010035187 A1 | 4/2010 | |
| WO | 2011004322 A1 | 1/2011 | |
| WO | 2013001411 A1 | 1/2013 | |
| WO | 2014083538 A1 | 6/2014 | |
| WO | WO-2014195146 A1 * | 12/2014 | ........... A61B 5/1117 |
| WO | 2015036245 A1 | 3/2015 | |
| WO | 2015091581 A1 | 6/2015 | |

OTHER PUBLICATIONS

Lee et al: "Analytical Review: Focus On Fall Screening Assessments"; American Academy of Physical Medicine and Rehabilitation; vol. 5, Jul. 2013, pp. 609-621.
PCT/EP02017/075718 ISR and Written Opinion, Dec. 14, 2017.

* cited by examiner

METHOD AND APPARATUS FOR DETERMINING A FALL RISK

CROSS REFERENCE TO PRIOR APPLICATIONS

This application is the U.S. National Phase application under 35 U.S.C § 371 or International Application No. PCT/EP2017/075718, filed on Oct. 10, 2017, which claims the benefit European Patent Application No. 16193433.6 filed on Oct. 12, 2016. These applications are hereby incorporated by reference in their entirety herein,

FIELD

The disclosure relates to a method and apparatus for determining the risk of a subject falling.

BACKGROUND

Falls are a significant problem., particularly for elderly people. About 30 percent of people over 65 years old fall at least once a year. Home-based fall-prevention exercise programs that include balance training, muscle strengthening, and a walking plan have been found to be effective in reducing the occurrence of falls by 30-46%. Fail risk assessment is important to identify elderly people at risk of falling, to tailor exercises for optimizing fall prevention intervention programs, and to monitor progression of fall risk.

In some cases, a subject can fill in a questionnaire to subjectively assess their fall risk. Based. on the answers the subject can get feedback in order to teach the subject how not to fall (e.g., to reduce their risk of falling).

Caregivers can provide a much better estimation of fall risk through objective assessment of physical performance (e.g., walking quality, strength, balance, and reaction time). The association between physical performance test outcomes and fall risk has been well established.

However, for objective fall risk assessment, people have to present themselves at a clinic where dedicated hardware and clinicians are needed. These tests are often obtrusive and require specific movements or activities to be performed. This results in a low monitoring/observation rate (e.g., perhaps only once a year). Moreover, subjects often present themselves for the first time to the clinic only after a fall occurred, i.e., when it is already too late.

It is therefore desirable to be able to monitor fall risk m the home environment. Systems for predicting fall risk based on measurements from one or more sensors that can be used in the home environment are known, for example, in U.S. Pat. No. 7,612,681. However, this monitoring can require obtrusive and expensive dedicated hardware, for example, a camera system or a network of other types of sensors that needs to be installed in the home.

Therefore, there is a need for an improved method and apparatus for determining a fall risk.

SUMMARY

The information gathered by one or more sensors in free living conditions (e.g., in the home environment) largely depends on the environmental challenges and the movement intention of the subject, which is not captured by the algorithm that evaluates the sensor measurements and determines the fall risk. It is therefore difficult to compare walking or other movements over time to measure changes in fall risk (e.g., in terms of ambulatory ability progression) since the context of the movements is different.

Thus, according to a first aspect, there is provided a computer-implemented method of determining a fall risk of a subject, the method comprising receiving a first data set indicative of movement of the subject; receiving a second data set indicative of context information of the subject; selecting a part of the first set based on the second data set; and determining a fall risk based on the selected part of the first data set.

According to a second aspect, there is provided a computer program product composing a computer readable medium having computer readable code embodied therein, the computer readable code being configured such that, on execution by a suitable computer or processor, the computer or processor is caused to perform the method of the first aspect.

According to a third aspect, there is provided an apparatus for determining a fall risk of a subject, the apparatus comprising a processing unit configured to receive a first data set indicative of movement of the subject; receive a second data set indicative of context information of the subject; select a part of the first data set based on the second data set; and determine a fall risk based on the selected 'art of the first data set.

BRIEF DESCRIPTION OF THE DRAWINGS

Exemplary embodiments of the invention will now be described, by way of example only, with reference to the following drawings, in which.

DETAILED DESCRIPTION OF EMBODIMENTS

As described above it is difficult to compare walking or other movements of a subject over time to measure changes in fall risk (e.g., in terms of ambulatory ability progression) since the context of the movements can be different at different times. For example, a subject may walk unaided during one time interval, and walk using a walking aid (such as a walking stick or walking frame) during another time interval, and thus it may not be appropriate to directly compare the subject's walking ability during each time interval (e.g., in assessing progression of fall risk, since the context of the walking is different).

Thus, embodiments provide that context information relating to movements of a subject is received or measured, and this context information is used to select a part of the measurements of the movements. A fall risk can then be determined from the selected part of the movement measurements. In this way, a large part of the variability between general types of movements (e.g. walking, jogging, standing still, exercising, sitting down, standing up, etc.) can be accounted for due to different contexts to the movements (e.g., using/not using a walking aid, moving in a well-lit/poorly-lit area, etc.), and thus the measure of fall risk determined. from the movement measurements can be more accurate, as well as provide a more accurate indication of the progression. or changes in fall risk over time.

Figure 1:
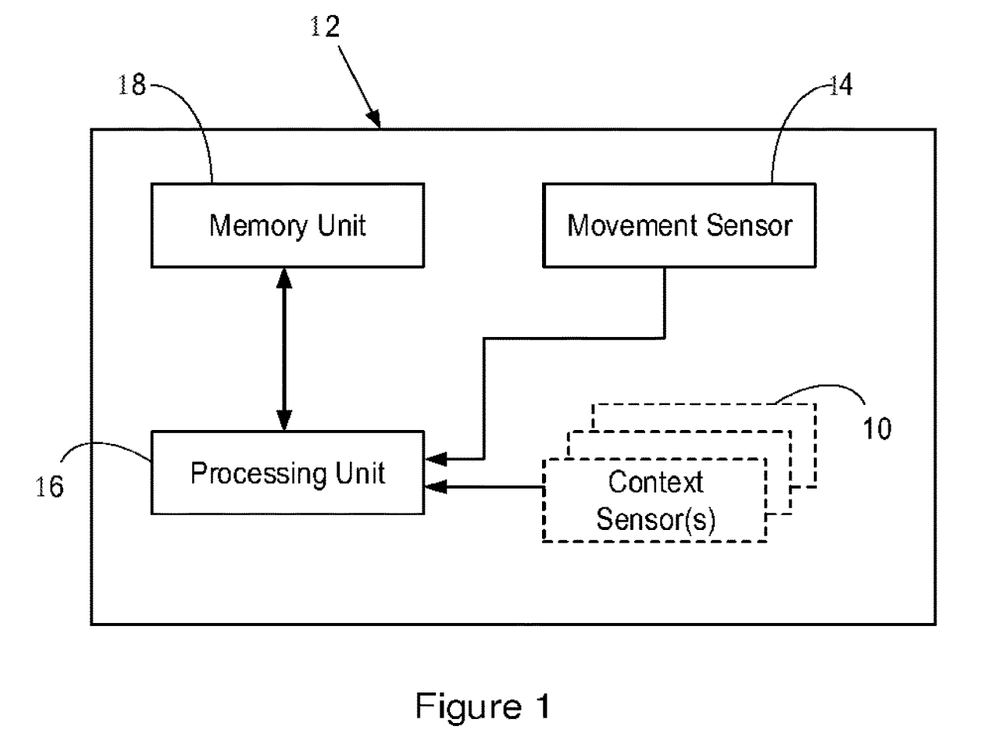
FIG. 1 is a block diagram of an apparatus according to an embodiment.

An embodiment of an apparatus 12 for determining a fall risk of a subject is shown in FIG. 1. The apparatus 12 comprises one or more movement sensors 14 that measure the movements or other motion of the subject. In some embodiments the movement sensor 14 is an accelerometer that measures accelerations ail three dimensions, in which case the movement sensor 14 can be worn or carried by the subject. The movement sensor 14 can comprise an altitude sensor (e.g., an air pressure sensor) that measures the altitude of the subject, or changes in the altitude or height of the subject (for example to determine if the subject has gone or is going up or down the stairs). The movement sensor 14 can comprise a position sensor for measuring the position of the subject. The position. sensor can be, for example, a satellite positioning system sensor, such as a GPS (Global Positioning System) receiver, that measures the location of the subject (and in some cases the speed of movement of the subject as well). The movement sensor 14 can comprise one or more cameras or other imaging devices that record images of the subject or the subject's surroundings, in which case the movement sensor 14 can be located in the environment of the subject. In some embodiments, the apparatus 12 can comprise multiple movement sensors (e.g., two or more of (and/or multiple instances of) an accelerometer, air pressure sensor, a position sensor, and an imaging device). Those skilled in the art will be aware of other types of movement sensor that can be used in an apparatus 12.

In the case of an accelerometer, the accelerometer can measure the magnitude of acceleration along three orthogonal axes (e.g., labelled X, Y, and Z) and output three signals, each representing the magnitude of acceleration along a respective one of the axes or output a single signal that is a composite of the accelerations measured along the three orthogonal axes. The accelerometer 14 (or more generally the movement sensor 14) can operate with any suitable sampling frequency, for example 50 Hz, i.e., the accelerometer 14 can output an acceleration measurement every $\frac{1}{50}$th of a second, or for example 10 Hz, The output of the movement sensor(s) 14 is referred to generally as a "first data set" herein and represents measurements of movements of the subject over time from each of the movement sensor(s) 14 (e.g., acceleration measurements from an accelerometer and air pressure measurements from an air pressure sensor).

The measurements of movements (first data set) are provided to a processing unit 16 in the apparatus 12. The processing unit 16 processes the measurements to determine a fall risk of the subject, as described in more detail below. The processing unit 16 also controls the operation of the apparatus 12, for example controlling the initiation of the collection of measurements by the movement sensor 14, and/or other functions and operations of the apparatus 12. The processing unit 16 can be implemented in numerous ways, with. software and/or hardware, to perform the various functions required. The processing unit 16 may comprise one or more microprocessors that may be programmed using software to perform the required functions. The processing unit 16 may be implemented as a combination of dedicated hardware to perform some functions and a processor (e.g., one or more programmed microprocessors and associated circuitry) to perform other functions. Examples of processing components that may be employed in various embodiments of the present disclosure include, but are not limited to, conventional microprocessors, application specific integrated circuits (ASICs), and field-programmable gate arrays (FPGAs). In some embodiments, components and functionality of the processing unit 16 can be distributed. across multiple locations in multiple units or modules, In various implementations, the processing unit 16 may be associated with one or more storage media, shown as memory unit 18 in FIG. 1. The memory unit 18 can be part of the processing unit 16, or it can be a separate component in the apparatus 12 that is connected to the processing unit 16. The memory unit 18 can comprise any suitable or desired type of volatile or non-volatile computer memory such as RAM. PROM, EPROM, and EEPROM. The memory unit 18 can be used for storing computer program code that can be executed by the processing unit 16 to perform the method described herein. The memory unit 18 can also be used to store signals or measurements from the movement sensor 14 and/or other sensors in the apparatus 12, and/or information relating to the fall risk determined by the processing unit 16.

As noted above, context information is used to identify a part of the movement measurements that are to be used to determine a fall risk. Thus, the apparatus 12 comprises one or more sensors that provides context information for the subject. In some embodiments, context information can be derived from the movement measurements from the movement sensor 14. In other embodiments, context information is also or alternatively provided by one or more context sensors 10. Generally, the context information is any type of information or measurement that can be used to determine the context sensors 10. Generally, the context information is any type of information or measurement that can be used to determine the context of movements by the subject.

Various examples of context sensor(s) 10, and the context information that can be measured by the context sensor(s) 10, are provided below. In some cases, the context sensor(s) 10 can monitor the environment around the subject (e.g., the lighting conditions, the ambient noise or sounds, or the location of the subject). In some cases, context sensor(s) 10 can be associated with an object or device that the subject may use, and the context sensor 10 can provide an indication of whether the object or device is being used by the subject. As such, a context sensor can itself be a 'movement sensor' (e.g., an accelerometer), but it is associated with a particular object or device rather than the subject, and thus measures the movements of the object or device. Suitable objects or devices include walking aids, medication dispensers, beds, etc. In some implementations, multiple context sensors 10 (of the same or different types) are located throughout the home environment of the subject so that may different activities and contexts of the subject can be measured. In these cases, the context sensors 10 may be part of an existing 'smart home' arrangement of devices and sensors.

An example of context information derived from the movement measurements from the movement sensor 14 is when an air pressure sensor measures a certain height change per step which can be interpreted as the subject climbing stairs with a certain steepness. Another example is where position measurements from a satellite positioning system indicate that the subject is outside on a track, a path (e.g., hill path) or a beach.

The measurements by the context sensor(s) 10 are provided to the processing unit 6 for use in determining the part of the first data set (movement measurements) that can be used to determine the fall risk. The context information (or more generally the measurement signals from the one or more context senor(s) 10) is referred to herein as a "second data set" and represents information on the context over time.

In some embodiments, all of the components of the apparatus 12 are part of the same device, e.g., the movement senor 14, context sensor(s) 10 and processing unit 16 are in a single housing. In these embodiments, the apparatus 12 can be portable or wearable so that it can be carried or worn by the subject. In some embodiments, the apparatus 13 is implemented in a fall detection system, in which case the processing unit 16 can be configured to both determine a fall risk from the first data set and second data set and determine whether the subject has suffered a fall from at least the first data set.

However, in other embodiments the movement sensor 14 and/or the context sensor(s) 10 are in a separate device or housing (or respective devices and housings) to the processing unit 16. Where the movement sensor 14 and/or context sensor(s) 10 are provided in a separate device(s) or housing(s) to the processing unit 16, appropriate circuitry or components can be provided to enable the movement measurements (first data set) and/or context information (second data set) to be sent (e.g., transmitted) to the processing unit 16. In some examples the movement sensor(s) 14 can be configured to be worn or carried by the subject (for example worn on their arm, leg, chest, waist, torso, or worn as a pendant around their neck). In these cases the processing unit 16 can, be part of a personal electronic device such as a smartphone, tablet computer, laptop computer or desktop computer, or part of another electronic device, such as a base unit or hub unit for the movement sensor 14, or part of a remote server (e.g. located in the cloud, i.e. accessible via the Internet), in which case the measurements from the movement sensor 14 can be sent wirelessly to the processing unit 16 in the electronic device using any suitable communication protocol (e.g., Wi-Fi, Bluetooth, or a cellular telecommunication protocol) so that the fall risk can be determined.

In some embodiments the processing unit 16 can receive the measurements from the movement sensor 14 and context sensor(s) 10 in real-time or near real-time (e.g., with the only delay being due to the signal processing required. to transmit or convey the measurements to the processing unit 16. In other embodiments (including embodiments where the movement sensor 14 and/or context sensor(s) 10 are separate From the processing unit 16, the measurements from the movement sensor 14 and/or context sensor(s) 10 can be stored in memory unit 18 and the processing unit 16 can retrieve and analyze the previously-obtained measurements from the memory unit 18 when a fall risk is to be determined.

As noted above, in some embodiments the processing unit 16 may be part of a smartphone or other general purpose computing device that can be connected to or otherwise receive a measurement signal from movement sensor 14 and context sensor(s) 10, but in other embodiments the apparatus 12 can be an apparatus that is dedicated to the purpose of determining a fall risk for a subject. in embodiments where the Processing unit 16 is part of a smartphone or other general purpose computing device, the movement sensor 14 could be the accelerometer and/or other type of movement sensor typically found in such a smartphone (e.g., a gyroscope).

It will be appreciated that FIG. 1 only shows the components required to illustrate various embodiments of the apparatus 12, and in a practical implementation the apparatus 12 will comprise additional components to those shown. For example, the apparatus 12 may comprise a. battery or other power supply for powering the apparatus 12, a. communication module foe enabling the information on a determined fall risk to be communicated to another device, e.g., a base unit for the apparatus 12 or a remote computer, a location or position sensor for determining the location or position of the apparatus 12 (and thus the subject), e.g. a Global Positioning System (GPS) receiver, and/or one or more user interface components that allow the subject or another user to interact and control the apparatus 12. As an example, the one or more user interface components could comprise a switch, a button or other control means for activating and deactivating the apparatus 12 and/or fall risk determination process. The user interface components can also or alternatively comprise a display or other visual indicator for providing information to the subject and/or other user about the operation of the apparatus 12, including displaying information on a determined fall risk, and/or information to educate the subject abut exercise, activities, or tasks to perform or avoid in order to reduce their fall risk.

Figure 2:
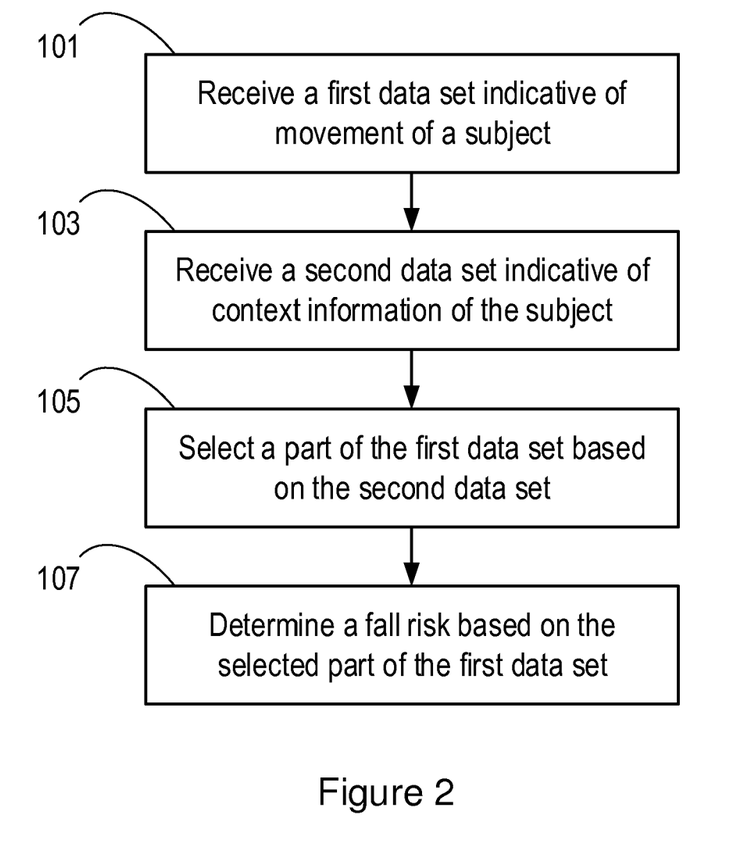
FIG. 2 is a flow chart illustrating a general method of determining a fall risk.

The flow chart in FIG. 2 illustrates a general method of determining a fall risk according to an embodiment. The method can be performed by processing unit 16.

In step 101, a first data set that is indicative of movement of the subject is received. The first data set contains measurements of movements of the subject over a period of time. The first data set is obtained by one or more movement sensors 14 that measure the movements of the subject. As noted above, the movement measurements can include measurements from multiple sensors, for example, acceleration measurements, position measurements, height/altitude measurements, camera images, etc. The first data set can be received directly from the movement sensor(s) 14 (e.g., in the case where the processing unit 16 and movement sensor(s) 14 are in the same or different devices), or the first data set can be retrieved from a memory unit 18. The former case is useful where the fall risk is to be determined in real-time or near real-time. The first data set may comprise the raw movement measurements, e.g., acceleration samples in the case of an accelerometer 14, or movement measurements that have been processed or filtered, e.g.,to remove noise and/or to identify the specific type of movements that the measurements relate to (e.g., walking, sitting, standing still, performing a sit to stand movement, etc.. In the latter case, those skilled in the art will be aware of various algorithms and techniques that can be used to identify those specific types of movements, and thus further details are not provided herein.

Figure 3:
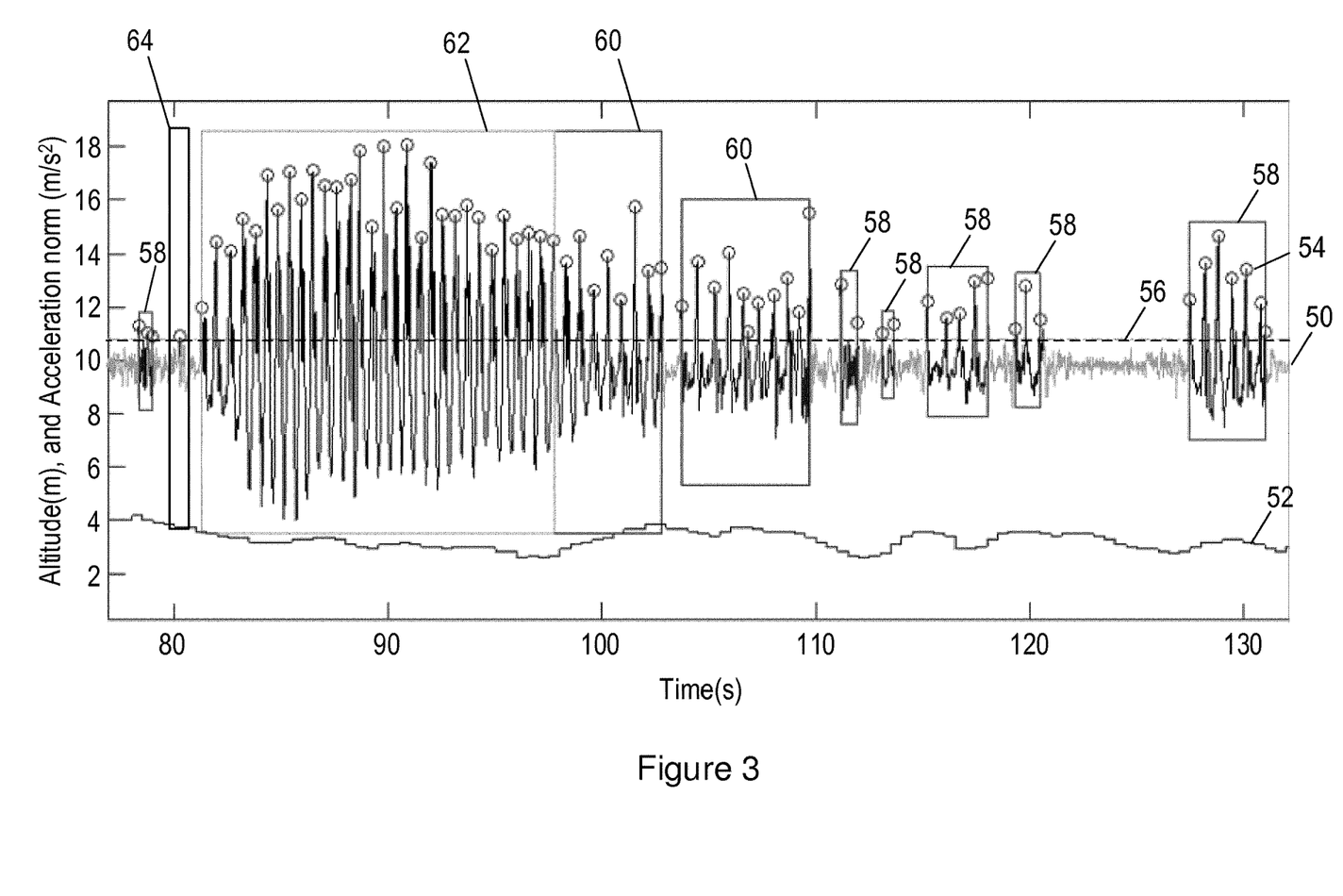
FIG. 3 illustrates a first data set indicative of movement of the subject.

FIG. 3 shows an example of a first data set that comprises acceleration measurements 50 and altitude measurements 52 obtained over a short time window of 130 seconds. It will of course be appreciated that in practice the first data set will cover a much larger time period, for example hours, days or weeks. The raw acceleration measurements are shown, but the altitude measurements 52 have been obtained from air pressure measurements. The results of some processing of the acceleration. measurements are shown in FIG. 3. with the circles 54 on various peaks in the acceleration measurements indicating where a step by the subject has been identified. A step may be identified, for example, where the magnitude of the acceleration exceeds a threshold (e.g., indicated by dashed line), although those skilled in the art will be aware of other algorithms or rules that can be used to identify steps. Where steps have been identified in the acceleration measurements, the steps and/or associated accelerations/movements have been further analyzed and four specific types of movements have been identified as shown by the boxes in FIG. 3. The first is shown by box 58 and represents the subject walking where there are three or more steps in a row that can be used for counting the subject's steps. The second is shown by box 60 which corresponds to the subject walking up and down stairs (which can also be seen in the altitude measurements). The third is shown by box 62 and represents the subject walking for some distance, and the measurements in this box 62 can be used to evaluate the subject's walking (e.g., for stride regularity, stride length, etc. The fourth is shown by box 64 and represents the subject getting up from a chair.

In step 103, a second. data set that is indicative of context information of the subject is received. Context information can be any type of information or measurement that can be used to determine the context of particular movements by the subject. The second data set, which can comprise measurements from one or more sensors 14./10, can be received directly from a sensor (e.g., the movement sensor 14 and/or one or more context sensors 10), or the second data set. can be retrieved from a memory unit 18. The second data set may comprise the raw sensor measurements, e.g., acceleration samples in the case of an accelerometer 14 or context measurement samples in the case of a context sensor 10, or measurements that have been processed or filtered, e.g., to remove noise and/or to identify the context over time. It will be appreciated that since the second data set is used to identify the context of the movements represented in the first data, set, the first data set and the second data set should contain measurements that at least cover the same time period. Thus, in the embodiments where the first data set and the second data set are received directly from the movement sensor 14 and optionally one or more context sensors 10), it will be appreciated that steps 101 and 103 are performed at the same time. In embodiments where the first data set and the second data set are received. from a memory unit 18, it will be appreciated that steps 101 and 103 can be performed at the same time, or at different times.

Figure 4:
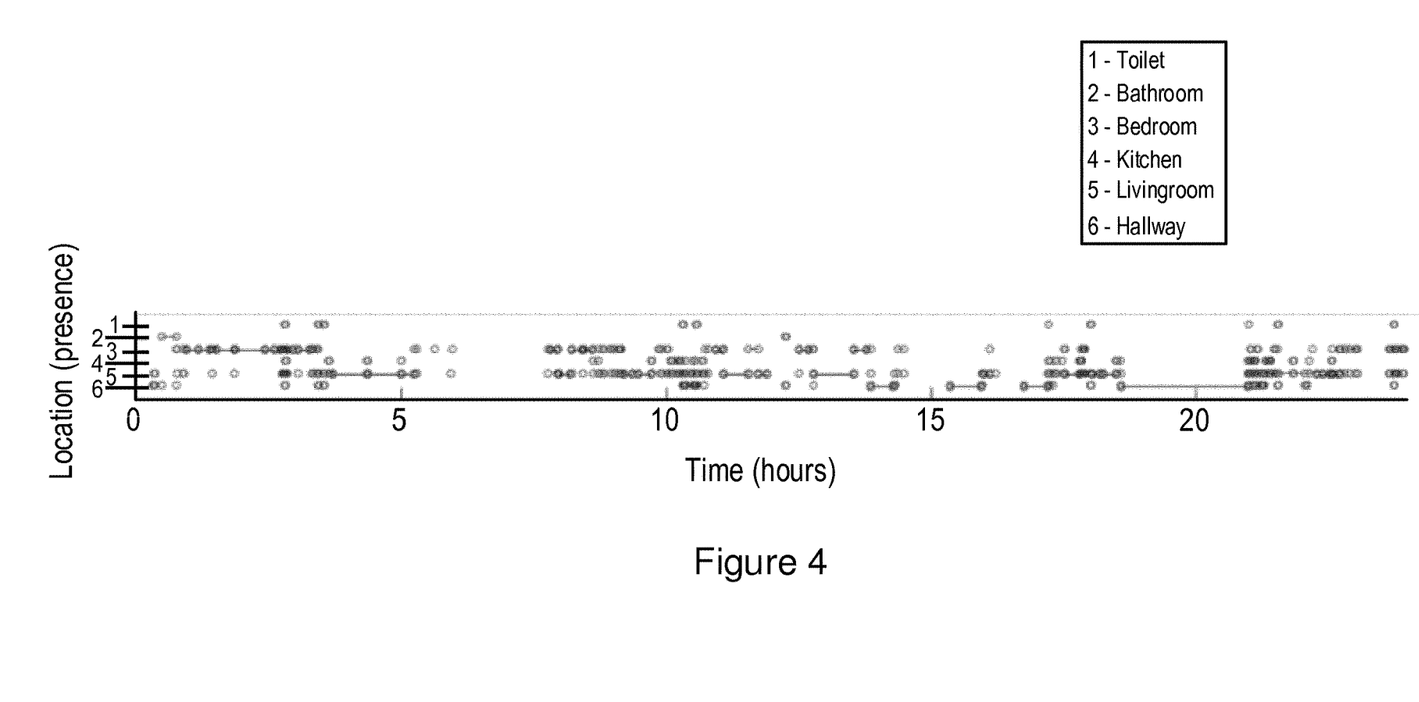
FIG. 4 illustrates a second data set indicative of context information of the subject.

FIG. 4 shows an example of -a second data set that comprises measurements from. a number of sensors 10 that detect the presence of the subject in a particular room over a period of one day (24 hours). It will of course be appreciated that in practice the second data set will cover a shorter or longer time period. The sensors 10 can be, for example, passive infrared, PIR, sensors positioned in each room. In this example, the second data set comprises presence measurements for the subject in six different rooms, namely the toilet 1, bathroom 2, bedroom 3, kitchen 4, living room 5, and hallway 6 with the sensor providing an 'on' signal when presence or movement is detected, and an 'off' signal when presence or movement is not detected. Typically, an 'off' signal occurs shortly after (e.g., a few seconds or minutes after an 'on' signal. A next 'on' signal may follow quickly if the subject is still present in that area/room. In FIG. 4, a series of closely following 'on' and 'off' signals are grouped into one line representing presence in the area/room.

Next, in step 105, as part of the first data set is selected based on the second data set. As noted above, there can be significant variability in the way that a subject performs or carves out a particular movement (e.g. walking, jogging, exercising, etc.), and. this variability can be accounted for due to the context being different for different instances of a particular movement (e.g. walking using a walking aid and walking unaided), and thus the context information in the second data set is used to select a part of the first data set that is to be used to determine the fall risk of the subject.

Where the first data set and/or the second data set received in steps 101/103 respective comprise raw sensor measurements, step 105 can comprise processing the movement measurements to identify the specific type of movements that the measurements relate to (e.g. walking, sitting, standing still, etc.) and/or processing the measurements to identify the context over time (although it will also be appreciated that some or all of this processing can be performed in steps 101/103 instead). As noted above, those skilled in the art will be aware of various algorithms and techniques that can be used to identify specific types of movements from movement measurements, and thus further details are not provided herein.

The part of the first data set selected in step 105 preferably relates to the same or similar context (as indicated by the second data set). Thus, for example, the part of the first data set selected in step 105 can be the movements where the lighting conditions are the same, where the movements are within the subject's home environment, where the subject is using a walking aid 7, etc.

As well as the same or similar context, the part of the first data set selected in step 105 preferably relates to the same or similar type of movement (as indicated by the first data set). Thus, for example, the part of the first data set selected in step 105 can be a. part determined to be walking movements by the subject where the context is the same or similar (e.g., same or similar lighting conditions).

It will be appreciated that the selected part of the first data set does not have to only comprise a single contiguous portion of the first data set, but instead the selected part can comprise several separate non-contiguous portions of the first data set. For example, the selected part can comprise any portion of the movement measurements that relate to walking in the same lighting conditions or walking with/without a walking aid 7. It will be appreciated that the portions of the movement measurements in the selected part of the first data set may cover movements that took place at different periods during a day, or during different days.

It will be appreciated that in. addition to the above, selected part of the first data set preferably relates to a type of movement or types of movements that are useful for determining a fall risk.

Figure 5:
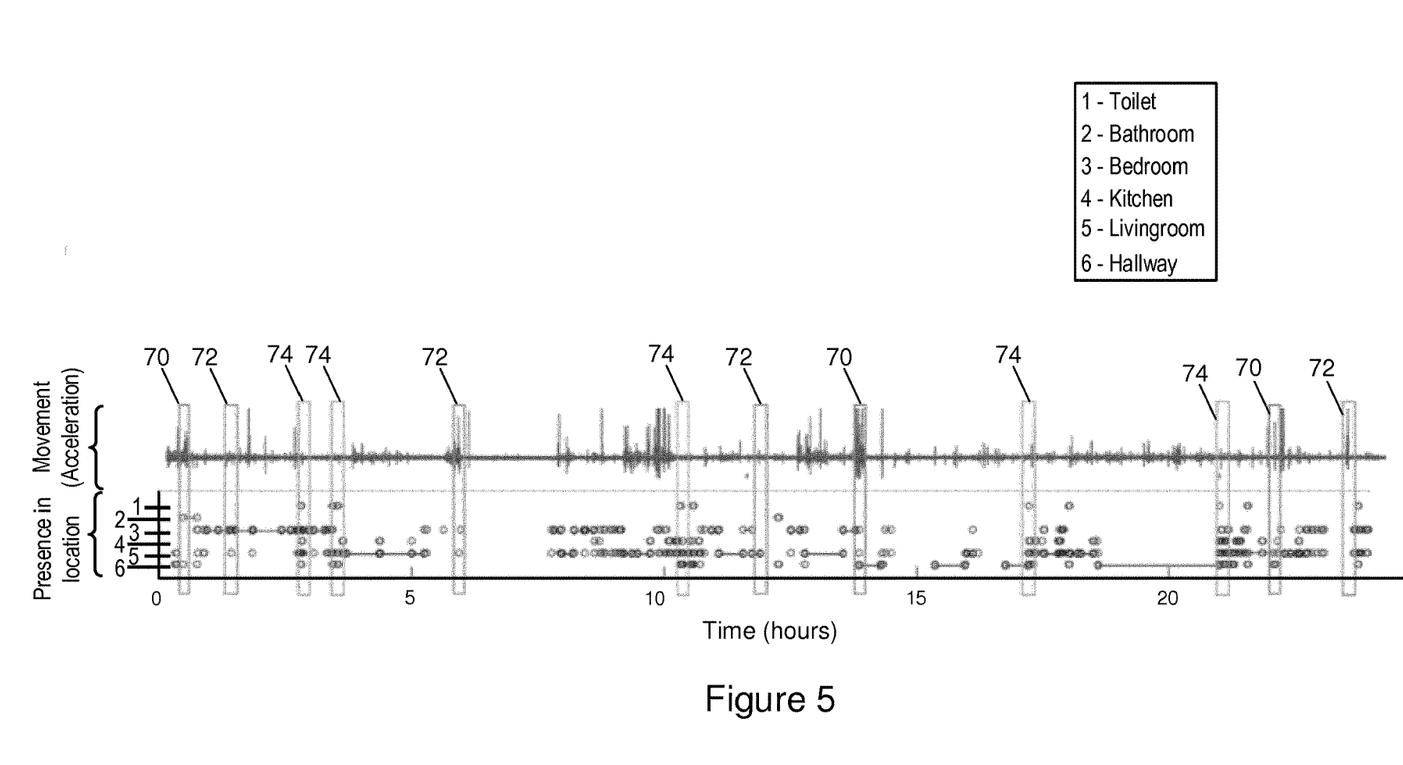
FIG. 5 illustrates a first data set and a second data and the selection of parts of the first data set.

FIG. 5 shows a first data set and a second data and the selection of parts of the first data set. in particular, FIG. 5 shows the second data set from FIG. 4 alongside a first data set that comprises acceleration measurements covering the same time period as the second data set. FIG. 5 shows three examples of a 'selected part' of the first data set that relate to the same or similar context and that can be used for determining a fall risk of the subject. in particular, the portions of the first data set labelled with box 70 relate to movement data where the subject is walking, as shown by the acceleration measurements, in the hallway 6, as shown by the context information (the presence information). Thus, the selected part of the first data set could correspond to portions 70, and these walking movements could be used to determine the fall risk. Alternatively, the portions of the first data set labelled with box 72 relate to movement data where the subject is getting up from a sitting position (i.e., a sit to stand movement) as shown by the acceleration measurements, in the lounge, as shown by the presence information, and therefore it can be implied that the subject is getting up from the same chair or same type of chair each time. Thus, the selected part of the first data set could correspond to portions 72. In another alternative, the portions of the first data set labelled with box 74 relate to movement data where the subject is getting up from a sitting position (i.e., a sit to stand movement), as shown by the acceleration measurements, in the toilet I, as shown by the presence information, and therefore it can be implied that the subject is getting up from the toilet I each time. Thus, the selected part of the first data set could correspond to portions 74.

Figure 6:
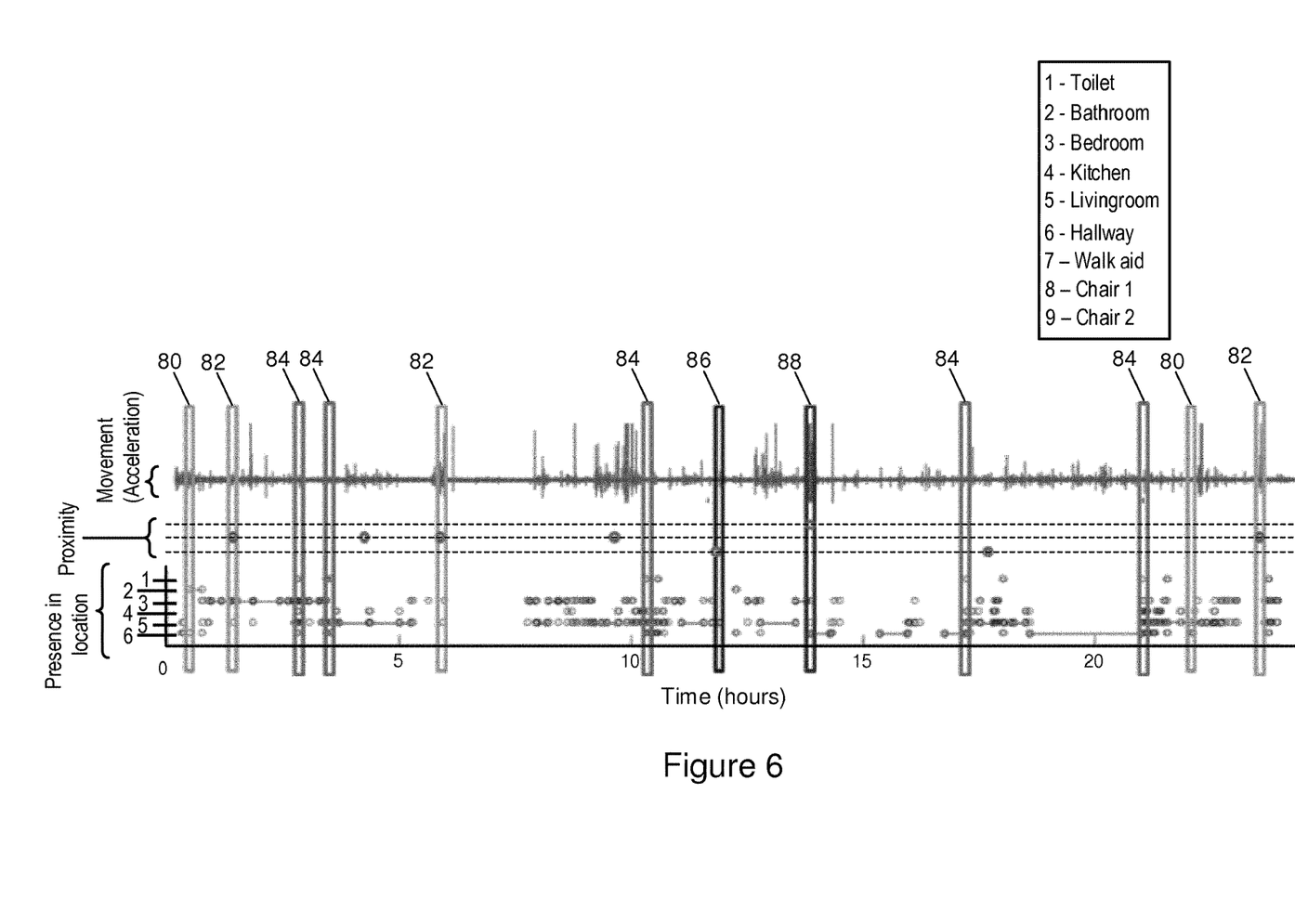
FIG. 6 illustrates a first data set and a second data set obtained from two different sensors and the selection of parts of the first data set.

FIG. 6 shows another example of a first data set and a second data set and the selection of parts of the first data set. In particular, FIG. 6 shows a first data set that comprises acceleration measurements (that is the same as the first data set in FIG. 5) and a second data set that comprises presence information (which is the same as in FIGS. 4 and 5) and proximity information that indicates whether the subject is proximate to (e.g., in contact with) a walking aid 7, a first chair 8 or a second chair 9. The second data set covers the same time period as the first data set. FIG. 6 shows five examples of a 'selected part' of the first data set that relate to the same or similar context and that can be used for determining a fall risk of the subject. These five examples correspond to the three examples shown in FIG. 5, with the chair rises being further delimited to the first chair 8 or the second chair 9 based on the p:roximity information, and the walking in the hallway 6 further delimited based on whether the subject is using a walking aid 7 or not (as indicated by the proximity information). In particular, the portions of the first data set labelled with box 80 relate to movement data where the subject is walking, as shown by the acceleration measurements, in the hallway 6, as shown by the context information (the presence information), with a walking aid 7, as shown by the proximity information. Thus, the selected part of the first data set could correspond to portions 80, and these walking movements (with a walking aid 7) could be used to determine the fall risk. Alternatively, the portions of the first data set labelled with box 82 relate to movement data where the subject is getting up from a sitting position (i.e. a sit to stand movement), as shown by the acceleration measurements, in the lounge, as shown by the presence information, and from the first chair (as shown by the proximity information) and therefore it is known that the subject is getting up from the same chair each tune. Thus, the selected part of the first data set could correspond to portions 82. In another alternative, the portions of the first data set labelled with box 84 relate to movement data where the subject is getting up from a sitting position (i.e., a sit to stand movement), as shown by the acceleration measurements, in the toilet 1, as shown by the presence information, and therefore it can be implied that the subject is getting up from the toilet I each time. Thus, the selected part of the first data set could correspond to portions 84. In yet another alternative, the portions of the first data set labelled with box 86 relate to movement data where the subject is getting up from. a sitting position (i.e. a sit to stand movement) as shown by the acceleration measurements, in the lounge, as shown by the presence information, and from the second chair 9 (as shown by the proximity information) and therefore it is known that the subject is getting up from the same chair (but different to portions 82) each time. As another alternative, the portions of the first data set labelled with 88 relate to movement data where the subject is walking, as shown by the acceleration measurements, in the hallway 6, as shown by the context information (the presence information), without using a walking aid 7, as shown by the proximity information. Thus, the selected part of the first data set could correspond to portions 88, and these walking movements (without a walking aid 7) could be used to determine the fall risk.

Once a part of the first data set has been selected, the fall risk of the subject is determined using the selected part of the first data set (step 107). Step 107 can be performed using conventional algorithms that determine fall risk from movement measurements. The particular algorithm that is used can depend on the type of movements covered by the selected part of the first data set. For example, where the selected part relates to walking (e.g., as covered by portions 70 in FIG. 5 or portions 80 in FIG. 6), the algorithm can be one that evaluates characteristics of walking to determine a fall risk. Exemplary techniques are described in WO 2010/026513 and WO 2011/04322. Where the selected part relates to sit to stand transfers (e.g., as covered by portions 72 or 74 in FIG. 5 or portions 82, 84 or 86 in FIG. 6), the algorithm can be one that evaluates characteristics of that type of movement to determine a fall risk. Exemplary techniques are described in WO 2010/035187, WO 2013/001411, and WO 2014/083538.

In some embodiments, the fall risk assessment can be based on changes in the performance of certain movements (e.g., walking, standing still, getting up from a chair, etc.) over time.

In some embodiments, the fail risk is determined only from the selected part of the first data set (i.e., the second data set is not used to determine the fall risk itself), but in other embodiments the fall risk is determined from the selected part of the first data set and the context information corresponding (in time) to the selected part of the first data set.

In some embodiments, the output of step 107 is a score that represents the subject's fall risk (e.g., a numerical score), a general indicator of fall risk (e.g., high, medium, or low), and/or an indicator of a change in fall risk over time (e.g., higher risk/lower risk).

Thus, the method in FIG. 2 provides that context information the second. data set) relating to movements of a subject is received or measured, and this context in is used to select a part or parts of measurements of the movements of the first data set). A fall risk. is then determined from the selected part of the movement measurements. In this way, it is possible to improve the reliability and sensitivity of the fall risk assessment since variability in the subject's movements (and thus variability in the determined fall risk) that is due to changes in the context of the movements can be excluded (or substantially excluded). It will be appreciated from the examples below that the use of the context information to select part of the first data set improves a fall risk derived from a relative assessment of different instances of the same type of movement (since those instances in the first data set will occur in the same context), and/or improve the absolute assessment of fall risk since the context of a specific movement can be taken into account by the fall risk assessment algorithm.

It will be appreciated that the method of FIG. 2 can be repeated (e.g., hourly, daily, weekly, etc.) in order to monitor the progression of the fall risk of the subject over time. The result of the fall risk assessment can be provided or indicated to the subject or a healthcare professional.

The context information used to select a part of the first data set as described above can also be used to provide information on the risk exposure of the subject (i.e., the likelihood of the subject falling), provide an indicator of the subject's mobility, and/or modify the interpretation of the subject's movement in relation to fall risk when determining the fall risk.

For example, in the case of a subject that is a frail elderly person recently discharged from hospital, it is useful to know whether the subject was using a walking aid 7 since this affects the subject's gait and balance. This context information can improve the fall risk assessment by providing information about the subject's: risk exposure (e.g. this subject is less likely to fall when walking if using the walking aid 7 compared to walking without using the walking aid 7); mobility indicator (e.g. subjects who need or feel the need to use a walking aid 7 have a. higher risk of falling compared to subjects not using a walking aid 7 at all, even if they have the same risk exposure); and change in movement pattern caused by the context (e.g. the use of a walking aid 7 changes movement patterns, which can be accounted for in the fall risk assessment of the walking movement).

Thus, as well as using the context information regarding the walking aid 7 to select only part of the first data set where the subject is walking and using a walking aid 7 (or alternatively is walking but not using a walking aid 7), the context information can be used by the fall risk assessment algorithm to interpret the quality of the walking movement appropriately.

As noted above, the sensor(s) 10 that obtain the context information can be sensors in a 'smart home' system (e.g., a system where many devices and objects in a home environment are interconnected and/or where the location and/or activities of a subject can be monitored). Such a system can use sensors, such as passive infrared (PIR) sensors and/or open-close (OC) sensors on doors, the refrigerator, etc. to monitor the location and activities of the subject. Alternatively or in addition, pressure mats (e.g. floor mats that include pressure sensors) can be placed on die floor to detect the presence of a subject in that room or location, and/or sensors on appliances or devices (e.g. on a kettle) can measure the activation and use of such an appliance or device.

Depending on the specific implementation, the sensors in the 'smart home' system may be able to provide context information on the 'activities of daily living' (ADL) of the subject. For example, the sensors can provide context information that allows the ADL to be inferred, such as the subject sleeping, the subject being present in a particular location/room, being out of the home environment, watching TV, eating and drinking, physical movements, sleep efficiency, using the toilet, bathing, and detecting visitors. These ADLs can be inferred from a pattern of events at various sensors, such as various PIR and OC sensors that are distributed around the home. For example, the subject leaving the house can be detected by a. combination of OC sensors mounted at the front (exit) door, and the presence of the subject before the OC event and no presence after that OC event, as measured by a PIR sensor in the hallway near to the door. Sleeping can be detected from a pressure mat that is located below the mattress of the subject's bed. Alternatively, measurements from a PIR. sensor in the bedroom 3 can be used to infer that the subject is sleeping. Eating and drinking, or meal preparation, can be inferred from detecting activity in the kitchen 4, measured by a PIR sensor in the kitchen 4, and/or with the usage of typical appliances like a refrigerator and a microwave, measured by OC sensors (or movement sensors) mounted to those appliances. Using the toilet 1 can be inferred from measurements by a PIR sensor in the toilet 1. Similarly, the subject bathing can be inferred from measurements by a PIR sensor in the bathroom 2.

Although the context sensor(s) described above are part of a 'smart home' system, it will be appreciated that these sensors can be provided just for the purposes of measuring context information for use in the method of FIG. 2.

Some specific examples of context information and/or devices or objects from which context information can be obtained that can be used to select the part of the first data set are set out below. It well be appreciated that any two or more of these examples can be used together or be part of the same apparatus.

Weighing scales—as well as providing a weight measurement of the subject, it can be useful to know when the subject was standing on the weighing scales since they will be aiming to stand upright and steady while the weight measurement is taken. The amount of body sway while the subject is standing on the weighing scales can be used to assess the fall risk (with, generally, higher body sway indicating a higher fall risk), and thus the weighing scales can comprise a context sensor 10 that outputs a second data set that indicates when the subject is standing on the weighing scales. In this case the context sensor 10 can be, for example, a pressure sensor located in, on or under the weighing scales, or a power sensor (in the case of electronic weighing scales). Alternatively, where the weighing scales are a 'connected' device (i.e., where measurements or sensor data can be communicated from the weighing scales to another device) the context sensor 10 can be the weight sensor in the weighing scales, The selected part of the first data set will be the portion(s) of the first data set that correspond in time to when the second data set indicates that the subject is standing on the weighing scales, Light sensor—it is useful to know the lighting conditions in the environment in which the subject is in, and to evaluate movements under the same lighting conditions when assessing fall risk. In low light the subject may be more unstable when walking than in bright light conditions. Thus, the context sensor 10 can be a light sensor that measures the light level. The light sensor could be worn or carried by the subject (in the same way as the movement sensor 14, or it could be located in the environment of the subject (in which case multiple light sensors may be provided in respective locations to provide light level measurements wherever the subject is located). In the latter case, a further sensor may be provided that can detect the presence of the subject in the location in which the light sensor is located. In this way, it is possible to determine where the subject is located and therefore which light sensor measurement should be used for the second data set. The presence sensor can be a PIR sensor, for example. The selected part of the first data set will be the portion(s) of the first data set where the light level is the same or similar(e.g., where each measurement is within a particular range). Preferably the selected part comprises the portion(s) of the first data set where the subject is performing a particular type of movement (e.g., walking, standing, etc.) and where the light level is the same or similar.

Walking aid 7—a walking aid 7 can be anything that helps a subject to walk or to walk more steadily than when unaided. A walking aid 7 can be a walking stick or a walking frame, for example. For fall risk assessment it is useful to know if the subject was using a walking aid 7, so that the fall risk assessment can be based on walking movements with a similar context (e.g., only walking is assessed where the subject is using a walking aid 7 or only walking is assessed where the subject is not using a walking aid 7). In some embodiments, as described above, the interpretation of the subject's movements by the fall risk assessment algorithm can be modified based on the indication of whether the subject is/was using a walking aid 7. Thus, in this example the context sensor 10 can be a movement sensor that is located on or in the walking aid. 7 and that indicates when the walking aid 7 is being moved. It will be appreciated in this case that the movement sensor on or in the walking aid 7 is a separate movement sensor to movement sensor 14 that measures the movements of the subject. Alternatively, the sensor 10 can be a sensor that detects contact or proximity between the subject and the walking aid 7, with contact (in conjunction with walking or other movements by the subject) being indicative of the walking aid 7 being used. A suitable sensor 10 m this case can be a skin conductance sensor or a pressure sensor on a handle of the walking aid 7. For a fall risk assessment based. on the subject's walking (or other movements) when the subject is using the walking aid 7, the selected part of the first data set will be the portion(s) of the first data set where the subject is walking (or performing other movements) and the second data set indicates that the walking aid 7 is also moving or being used. For a fall risk assessment based on the subject's walking (or other movements) when the subject is not using the walking aid 7, the selected part of the first data set will be the portion(s) of the first data set where the subject is walking (or performing other movements) and the second data set indicates that the walking aid 7 is not being moved or used. It will be appreciated that in either case the fall risk can be assessed based on an estimation of gait stability (e.g., by determining Lyapunov exponents or footstep time variance) or by estimating gait regularity from the movement: measurements. It will also be appreciated that a fall risk can be assessed using these estimations for walking without any information about the use or non-use of a walking aid 7. In some embodiments, the fall risk assessment may comprise determining a fall risk when the subject is not using the walking aid 7, determining a fall risk when the subject is using the walking did 7, and. comparing the two determined fall risks. This comparison would show the level of dependence of the subject on the walking aid 7, and/or the effectiveness of the use of the walking aid 7 to reduce fall risk.

Bed—it is useful to know when the subject has got out of bed since getting up quickly after a long period in bed is associated with. an immediate drop in blood. pressure and thus dizziness (it will be appreciated that this is also applicable to getting up from a chair). In addition or alternatively, it can be useful to know the length of time that the subject has been in bed, since the amount and/or quality of sleep that the subject has had can impact their fall risk (typically more tired means that they are at a higher risk of falling). Thus, the context sensor 10 can be used to determine or detect the presence and/or movements of the subject in bed. In this case the context sensor 10 can be a pressure sensor that is positioned on or in the bed. (e.g., below a mattress), or a sensor that can observe the movement of the subject in their bedroom 3 (e.g., a camera. or imaging device, with the images being processed to identify the posture and/or movements of the subject. Alternatively, a separate context sensor 10 may not be required as a 'getting-up-from-bed' movement can be detected in the movement measurements from the movement sensor 14. The selected part of the first data set can be the portion of the first data set where the subject is out of bed, alternatively where the subject has just got out of bed, or alternatively at least a predetermined amount of time after the subject has got out of bed. In some embodiments, the length of time since the subject got out of bed can be used as an indicator of how tired the subject is, and in this case the selected part of the first data set can be movements where the subject has the same or a similar level of tiredness (e.g., the same or a similar length of time since the subject got out of bed.

Chair 8—one way in which fall risk can be assessed is from the subject's ability to stand up from sitting on a chair 8 (known as a sit to stand transfer (STS)) However, chairs 8/9 can be of different sizes and shapes, and include/not include arm rests, etc., so it is useful to identify the chair 8 that the subject was sitting on. Thus, the context sensor 10 can be a sensor that measures the presence of a subject in a particular chair 8, and the selected part of the first data set can be the portion(s) of the first data set corresponding to a sit to stand movement where the subject was sitting on the same chair 8, or same type of chair. This allows the STS movements to be compared when assessing the fall risk.

Toilet 1—this is similar to the chair embodiment above in that a sit to stand movement from. the toilet 1 can be assessed, and thus is useful to know when a sit to stand movement from a toilet: 1 occurred. In this case the context sensor 10 can be a sensor that detects the presence of the subject in a bathroom 2 and/or detects that the subject sat on the toilet 1.

Hallway/corridor 6—subject will typically walk in a straight line down a hallway 6 or corridor, and it can be useful to assess the fall risk of the subject from this walking (specifically the gait stability and/or gait regularity) since the walking 'scenario' is consistent (e.g. similar walk length, similar location, restricted options for where to walk., similar walking intention. (e.g. walking to the kitchen 4, etc.). In this case the context sensor 10 can be a sensor that detects the presence of the subject in the hallway 6 or corridor, and for example the sensor 10 can be a PIR sensor, pressure sensor (e.g., located in or on the floor) or an imaging unit (e.g., camera). Thus, the selected part of the first data set can be the portion(s) in which the subject is located in the hallway 6 or corridor. Alternatively, the selected part of the first data set can be the portion(s) in which the subject is determined to be located in the hallway 6 or corridor and is determined to be walking. Further useful context information can be provided by a light sensor that measures the light level in the hallway 6 or corridor, and thus the selected part of the first data set can further correspond to walking in similar lighting conditions.

Medication dispenser—the fall risk of a subject may depend on any medication that they are taking (or not, if they have missed a dose). For example, blood pressure medication, anti-depressants and medication for Parkinson's disease have an influence on the ambulatory ability of the subject, and thus it is useful to know if the subject has recently or is consistently taking certain types of medication. Thus, where the subject obtains the medication from a medication dispenser (e.g., a device that stores their medication and dispenses the required dose at a required timed), the context sensor 10 can be a sensor that detects when a dose of medication has been removed from the medication dispenser and/or a sensor that detects the type of medication that has been dispensed. The selected part of the first data set can be the portion(s) of the movements of the subject where the subject has taken the same type of medication and/or the portion(s) where the subject took the medication a certain time period previously (e.g., more than one hour ago, etc.).

Ambient noise or sound level—the noise or sound level around the subject can provide an indication of how distracted the subject is (e.g., they are talking/being talked to, traffic noise, tone of the voice of the person, silence, etc.)

Other examples of context information. include the location, e.g. measured using GB, In which case the selected part may correspond to movements in the same or similar location, or movements following the same path, the weather conditions or temperature, in which case the selected part may correspond to those movements where the weather is the same or the temperature is the same (or within a predetermined range), the time of day, in which case the selected part may correspond to those movements during the same or a similar time of day, e.g. in the morning, afternoon, etc.

There is therefore provided an improved method and apparatus for determining a fall risk.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. in the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measures cannot he used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of determining a fall risk of a subject, the computer-implemented method when executed on a processing unit causes the processing unit to perform operations comprising:
    performing a fall risk assessment by:
        receiving, from a movement sensor, a first data set containing continuous measurements of movements of the subject over a continuous period of time;
        receiving, from a context sensor different from the movement sensor, a second data set indicative of context information of the subject that can be used to determine a context of particular movements of the subject, wherein the second data set contains continuous measurements that cover the continuous period of time covered by the first data set;
        determining two or more contexts from the context information of the second data set, each context of the two or more contexts including at least two temporal occurrences over the continuous period of time;
        selecting a context from the two or more contexts to determine a fall risk of the subject for the selected context;
        selecting a part of the first data set based on the selected context, the selected part of the first data set comprising a plurality of separate, non-contiguous portions of the first data set, wherein selecting the part of the first data set comprises, for each temporal occurrence of the selected context of the second data set:
            determining a respective interval within the continuous period of time corresponding to the respective temporal occurrence; and
            selecting a portion of the first data set at the respective interval within the continuous period of time of the first data set; and
        determining the fall risk of the subject for the selected context based on movement measurements in the selected part of the first data set;
    periodically repeating performance of the fall risk assessment to update the fall risk of the subject for the selected context; and
    transmitting, from the processing unit to a client device, for display in a user interface of the client device, one or more visual indicators comprising one or more tasks for the subject to perform to reduce the determined fall risk of the subject for the selected context, the one or more visual indicators based on the determined fall risk of the subject for the selected context.

2. The computer-implemented method as claimed in claim 1, wherein the step of selecting further comprises:
    selecting a context that corresponds to a fall risk.

3. The computer-implemented method as claimed in claim 1, wherein the operations further comprise:
    processing the first data set to identify occurrences of a particular type of movement performed by the subject,
    wherein selecting the context from the two or more contexts comprises using the second data set to select the context from the two or more contexts that relates to the particular type of movement.

4. The computer-implemented method as claimed in claim 3, wherein the particular type of movement comprises at least one of walking, jogging, running, getting up from a sitting position, exercising, or standing still.

5. The computer-implemented method as claimed in claim 1, wherein the context information comprises any one or more of a location of the subject, a light level, whether the subject is using a walking aid, whether or when the subject is in bed, whether or when the subject is standing still, whether the subject is using a specific chair, whether or when the subject is using a toilet, whether or when the subject has taken medication, a temperature, weather conditions, or a time of day.

6. The computer-implemented method as claimed in claim 1, wherein the operations further comprise measuring, with the movement sensor, the movements of the subject to provide the first data set.

7. The computer-implemented method as claimed in claim 1, wherein the operations further comprise measuring, with the context sensor, context information of the subject to provide the second data set.

8. A non-transitory computer readable medium having computer readable code embodied therein, the computer readable code being configured such that, on execution by a processor, the processor is caused to perform a method of determining a fall risk of a subject, the non-transitory computer readable medium comprising:
    instructions for performing a fall risk assessment by:
        receiving, from a movement sensor, a first data set containing measurements of movements of the subject over a continuous period of time;
        receiving, from a context sensor different from the movement sensor, a second data set indicative of context information of the subject that can be used to determine a context of particular movements of the subject, wherein the second data set contains measurements that cover the continuous period of time covered by the first data set;
        determining two or more contexts from the context information of the second data set, each context of the two or more contexts including at least two temporal occurrences over the continuous period of time;

selecting a context from the two or more contexts to determine a fall risk of the subject for the selected context;

selecting a part of the first data set based on the selected context, the selected part of the first data set comprising a plurality of separate, non-contiguous portions of the first data set, wherein selecting the part of the first data set comprises, for each temporal occurrence of the selected context of the second data set:

determining a respective interval within the continuous period of time corresponding to the respective temporal occurrence; and selecting a portion of the first data set at the respective interval within the continuous period of time of the first data set; and determining the fall risk of the subject for the selected context based on movement measurements in the selected part of the first data set;

instructions for periodically repeating performance of the fall risk assessment to update the fall risk of the subject for the selected context; and instructions for transmitting, from the processor to a client device, for display in a user interface of the client device, one or more visual indicators comprising one or more tasks for reducing the determined fall risk of the subject for the selected context, the one or more visual indicators based on the determined fall risk of the subject for the selected context.

9. An apparatus for determining a fall risk of a subject, the apparatus comprising:

a processor configured to:

perform a fall risk assessment by:

receiving, from a movement sensor, a first data set containing measurements of movements of the subject over a continuous period of time;

receiving, from a context sensor different from the movement sensor, a second data set indicative of context information of the subject that can be used to determine a context of particular movements of the subject, wherein the second data set contains measurements that cover the continuous period of time covered by the first data set;

determining two or more contexts from the context information of the second data set, each context of the two or more contexts including at least two temporal occurrences over the continuous period of time;

selecting a context from the two or more contexts to determine a fall risk of the subject for the selected context;

selecting a part of the first data set based on the selected context, the selected part of the first data set comprising a plurality of separate, non-contiguous portions of the first data set, wherein selecting the part of the first data set comprises, for each temporal occurrence of the selected context of the second data set:

determining a respective interval within the continuous period of time corresponding to the respective temporal occurrence; and selecting a portion of the first data set at the respective interval within the continuous period of time of the first data set; and determining the fall risk of the subject for the selected context based on movement measurements in the selected part of the first data set;

periodically repeat performance of the fall risk assessment to update the fall risk of the subject for the selected context; and transmitting, from the processor to a client device, for display in a user interface of the client device, one or more visual indicators comprising one or more tasks for the subject to perform to reduce the determined fall risk of the subject for the selected context, the one or more visual indicators based on the determined fall risk of the subject for the selected context.

10. The apparatus as claimed in claim 9, wherein the processor is configured to select a context that corresponds to a fall risk.

11. The apparatus as claimed in claim 9, wherein the processor is configured to:

process the first data set to identify occurrences of a particular type of movement performed by the subject; and select the part of the first data set by using the second data set to select the context that relates to the particular type of movement.

12. The apparatus as claimed in claim 11, wherein the particular type of movement comprises at least one of walking, jogging, running, getting up from a sitting position, exercising, or standing still.

13. The apparatus as claimed in claim 9, wherein the context information comprises any one or more of a location of the subject, a light level, whether the subject is using a walking aid, whether or when the subject is in bed, whether or when the subject is standing still, whether the subject is using a specific chair, whether or when the subject is using a toilet, whether or when the subject has taken medication, a temperature, weather conditions, or a time of day.

* * * * *